(12) United States Patent
Wang

(10) Patent No.: US 11,812,752 B2
(45) Date of Patent: Nov. 14, 2023

(54) EFFECTIVE DISINFECTANT SYSTEM FOR ELIMINATION OF RNA VIRUSES

(71) Applicant: Liming Wang, Solon, OH (US)

(72) Inventor: Liming Wang, Solon, OH (US)

(*) Notice: Subject to any disclaimer, the term of this patent is extended or adjusted under 35 U.S.C. 154(b) by 270 days.

(21) Appl. No.: 16/858,700

(22) Filed: Apr. 26, 2020

(65) Prior Publication Data
US 2021/0329926 A1 Oct. 28, 2021

(51) Int. Cl.
*A01N 63/50* (2020.01)
*C12N 9/22* (2006.01)
*C12N 9/64* (2006.01)
*C12N 9/76* (2006.01)

(52) U.S. Cl.
CPC ............ *A01N 63/50* (2020.01); *C12N 9/22* (2013.01); *C12N 9/6424* (2013.01); *C12N 9/6427* (2013.01); *C12Y 304/21004* (2013.01); *C12Y 304/21064* (2013.01)

(58) Field of Classification Search
CPC .......... A01N 63/60; A01N 63/50; C12N 9/22; C12N 9/6424; C12N 9/6427; C12Y 304/21004; C12Y 304/21064
See application file for complete search history.

(56) References Cited

U.S. PATENT DOCUMENTS

2002/0172949 A1* 11/2002 Gautsch et al. ................. 435/6

OTHER PUBLICATIONS

Farcet et al., "Development of a Triton X-100 replacement for effective virus Inactivation in biotechnology processes", Engineering Reports, 2019;1:e12078 (DOI: 10.1002/eng2.12078); (Total pp. 1-10). (Year: 2019).*
Chen N, et al. (Feb. 2020). Epidemiological and clinical characteristics of 99 cases of 2019 novel coronavirus pneumonia in Wuhan, China: a descriptive study. Lancet. 395 (10223): 507-513 Q&A on coronaviruses. World Health Organization. Apr. 8, 2020 Symptoms of Coronavirus. U.S. Centers for Disease Control and Prevention. Mar. 20, 2020.
Hui DS, et al. (Feb. 2020). The continuing 2019-nCoV epidemic threat of novel coronaviruses to global health—The latest 2019 novel coronavirus outbreak in Wuhan, China. Int J Infect Dis. 91: 264 66 New coronavirus stable for hours on surfaces. National Institutes of Health. Mar. 17, 2020. Archived from the original on Mar. 23, 2020. Retrieved Mar. 23, 2020.
Doremalen NJ, et al. (Apr. 16, 2020). Aerosol and Surface Stability of SARS-CoV-2 as Compared with SARS-CoV-1. New England Journal of Medicine 382:1564-1567.
Salehi S, et al (Mar. 14, 2020). Coronavirus Disease 2019 (COVID-19): A Systematic Review of Imaging Findings in 919 Patients. American Journal of Roentgenology: 1-7.
Lai C, et al (Mar. 1, 2020). Severe acute respiratory syndrome coronavirus 2 (SARS-CoV-2) and coronavirus disease—2019 (COVID-19): The epidemic and the challenges. International Journal of Antimicrobial Agents. 55 (3): 105924.
Lauer SA et al (Mar. 10, 2020). The Incubation Period of Coronavirus Disease 2019 (COVID-19) From Publicly Reported Confirmed Cases: Estimation and Application. Annals of Internal Medicine. doi:10.7326/M20-0504. Retrieved Mar. 24, 2020.
Bai Y et al (Feb. 21, 2020). Presumed Asymptomatic Carrier Transmission of COVID-19. JAMA. 323 (14): 1406 Outbreak of severe acute respiratory syndrome coronavirus 2 (SARS-CoV-2): increased transmission beyond China—fourth update. European Centre for Disease Prevention and Control. Feb. 14, 2020. Retrieved Mar. 8, 2020.
Andersen KG et al (Mar. 17, 2020). The proximal origin of SARS-CoV-2. Nature Medicine. 26 (4): 450-452.
Zhu N et al. (Feb. 2020). A Novel Coronavirus from Patients with Pneumonia in China, 2019. The New England Journal of Medicine. 382 (8): 727-733 Coronavirus Disease 2019 (COVID-19)—Transmission. Centers for Disease Control and Prevention. Mar. 17, 2020. Retrieved Mar. 23, 2020. Q&A on coronaviruses. World Health Organization. Feb. 11, 2020. Retrieved Apr. 13, 2020.
Collin EA et al (2015). Cocirculation of two distinct genetic and antigenic lineages of proposed influenza D virus in cattle. J Virol. 89 (2): 1036-42 Influenza (Seasonal). World Health Organization. Nov. 6, 2018. Archived from the original on Nov. 30, 2019. Retrieved Nov. 30, 2019.
Jefferson I et al. (Jul. 2011). Physical interventions to interrupt or reduce the spread of respiratory viruses. Cochrane Database Syst Rev (7): CD006207 Up to 650 000 people die of respiratory diseases linked to seasonal flu each year. World Health Organization (Press release). Dec. 14, 2017. Archived from the original on Apr. 18, 2019. Retrieved Sep. 24, 2019. Types of Influenza Viruses Seasonal Influenza (Flu). Centers for Disease Control and Prevention. Sep. 27, 2017.
Mills CE et al (Dec. 2004). Transmissibility of 1918 pandemic influenza. Nature. 432 (7019): 904-6.
Taubenberger JK et al (Jan. 2006). 1918 Influenza: the mother of all pandemics. Emerging Infectious Diseases. 12 (1): 15-22. Report of the Review Committee on the Functioning of the International Health Regulations (2005) in relation to Pandemic (H1N1) 2009. World Health Organization. May 5, 2011. p. 37. Archived from the original on May 14, 2015.

(Continued)

*Primary Examiner* — Satyendra K Singh
(74) *Attorney, Agent, or Firm* — Ashley D. Johnson; Dogwood Patent and Trademark Law

(57) ABSTRACT

Pandemic COVID 19 causes global crisis in human health and economy. The pathogen of COVID 19, like the Influenzas causing common flus, belongs to a common type of virus called Ribonucleic Acid (RNA) virus. RNA viruses are composed of three structural components: genomic RNA, envelop and nuclear proteins, and bilayer lipid membrane. Targeting COVID 19 and all RNA viruses, the present invention describes an effective disinfectant system, which applies the combination of RNases, proteases, and detergents, at a broad range of concentration, pH, and temperature in the utilization, to eliminate the RNA viruses from any contaminated surfaces, airways, and filters. The disinfectant system provides an effective, convenient, environment friendly, and safe solution, for commercial and customer use, to disinfect RNA virus pathogens in concern.

8 Claims, 3 Drawing Sheets

(56) References Cited

OTHER PUBLICATIONS

Dawood FS et al. (Sep. 2012). Estimated global mortality associated with the first 12 months of 2009 pandemic influenza A H1N1 virus circulation: a modelling study. The Lancet. Infectious Diseases. 12 (9): 687-95.

Cuchillo CM et al (Sep. 2011). Bovine pancreatic ribonuclease: fifty years of the first enzymatic reaction mechanism. Biochemistry. 50 (37): 7835-41.

King JV et al (Jul. 8, 2014). "Molecular basis of substrate recognition and degradation by human presequence protease". Structure. 22 (7): 996-1007.

Shen Y et al (Oct. 19, 2006). "Structures of human insulin-degrading enzyme reveal a new substrate recognition mechanism". Nature. 443 (7113): 870-874.

Luche S et al (2003). Evaluation of nonionic and zwitterionic detergents as membrane protein solubilizers in two-dimensional electrophoresis. Proteomics. 3: 249-53.

Chae P et al. (2012) A new class of amphiphiles bearing rigid hydrophobic groups for solubilization and stabilization of membrane proteins. Chemistry.18:9485-90.

Morihara K et al (1975). Specificity of proteinase K from Tritirachium album Limber for synthetic peptides. Agric. Biol. Chem. 39 (7): 1489-1492.

Hilz H et al (1975). Stimulation of Proteinase K action by denaturing agents: application to the isolation of nucleic acids and the degradation of 'masked' proteins. European Journal of Biochemistry. 56 (1): 103-108.

Johnson M (2018). Detergents: Triton X-100, Tween-20, and More. Materials and Methods. 3: 163-72.

Farcet JB et al (Dec. 12, 2019). Development of a Triton X-100 replacement for effective virus inactivation in biotechnology processes. Engineering Reports. 1 (5). Authorization List. European Chemicals Agency. Retrieved Dec. 14, 2019.

Koley D et al (2010). Triton X-100 concentration effects on membrane permeability of a single HeLa cell by scanning electrochemical microscopy (SECM). Proc. Natl. Acad. Sci. U.S.A. 107 (39): 16783-7.

Sinha S et al (2017). Use of substitute Nonidet P-40 nonionic detergents in intracellular tubulin polymerization assays for screening of microtubule targeting agents. Biochemistry and Cell Biology. 95 (3): 379-384.

\* cited by examiner

EFFECTIVE DISINFECTANT SYSTEM FOR ELIMINATION OF RNA VIRUSES

FIELD OF INVENTION

The present invention is the creation of disinfectants composed the combinations of Ribonucleases (RNases), Protein cleavage enzymes (Proteases) and detergents (ionic and non-ionic) which are suitable for commercial and customer use in disinfecting various surfaces, airways, and filters to effectively eliminate and destroy all natural and/or naturally derived Ribonucleic Acid (RNA) viruses, including severe acute respiratory syndrome coronavirus 2, or SARS-CoV-2 (pathogen of COVID 19), and Influenzas. The disinfectants are effective, convenient, environment friendly, safe, and easy to use.

BACKGROUND OF THE INVENTION

First identified in Wuhan China, Coronavirus disease 2019 (COVID-19) is an infectious disease caused by severe acute respiratory syndrome coronavirus 2 (SARS-CoV-2). Those infected with the virus may be asymptomatic or develop flu-like symptoms, including fever, cough, fatigue, and shortness of breath. Emergency symptoms include difficulty breathing, persistent chest pain or pressure, confusion. Currently, there is no vaccine or specific antiviral treatment available.

Current Pandemic COVID 19 is causing global crisis in human health. With more than 180 nations involved, there are over 2.8 million people infected, over 180,000 lives lost, COVID 19 spread rapidly, and in certain populations, deadly.

The virus is mainly spread during close contact, and by small droplets produced when people cough, sneeze, or talk, then land in the mouths or noses of people who are nearby or possibly be inhaled into the lungs. New data suggest the virus spread is possibly airborne. FIG. 1.

People may also catch COVID-19 by touching a contaminated surface and then their face. The virus can survive on surfaces up to 72 hours. Extreme case indicated the virus can be detected after 17 days.

Common flu, another major health threatening disease, is an infectious disease caused by an influenza virus. Influenza spreads around the world in yearly outbreaks, resulting in about three to five million cases of severe illness and about 290,000 to 650,000 deaths. The spread path is similar to SARS-CoV-2 virus.

In the 20th century, three influenza pandemics occurred: Spanish flu in 1918 (17-100 million deaths), Asian flu in 1957 (two million deaths), and Hong Kong flu in 1968 (one million deaths). The World Health Organization declared an outbreak of a new type of influenza A/H1N1 to be a pandemic in June 2009.

There are 7 known corona viruses can infect human, including HCoV-229E` HCoV-OC43 HCoV-NL63` HCoV-HKU1` SARS-CoV, MERS-CoV, and SARS-CoV-2. A schematic structure of COVID 19 virus is shown in FIG. 2.

Three of the four types of influenza viruses affect human: Type A, Type B, and Type C. A schematic structure of Influenza virus is shown in FIG. 3.

Both COVID 19 and Flus are caused by a common type of virus called Ribonucleic Acid (RNA) virus. RNA viruses generally have very high mutation rates. This is the main reason why it is difficult to make effective vaccines to prevent these diseases.

Intact RNA viruses are composed of three structural components: genomic RNA, envelop and nuclear proteins, and bilayer lipid membrane.

Destroy the three parts of components will break down and disrupt the intact virus; therefore prevent viral infection of human cells.

Apart from commonly used disinfectants composed of synthetic chemicals, the current embodiment applies environment friendly biological molecules to eliminate the RNA viruses. The components of this invention are described as following.

Ribonucleases (RNases) are a big family of hydrolytic enzymes that degrade RNA molecules. RNases catalyze the breakdown of RNA into smaller components.

Proteases (also called peptidase or proteinase) are a group of enzymes that catalyzes proteolysis, the breakdown of proteins into smaller polypeptides or single amino acids. They do this by cleaving the peptide bonds within proteins by hydrolysis, a reaction where water breaks bonds.

One feature of proteases is its autolysis. Proteases, being themselves proteins, are cleaved by other protease molecules, sometimes of the same variety. This makes the biological usage of proteases safe to the living organisms and environment.

Detergents are amphiphilic molecules, containing both hydrophilic and hydrophobic regions. This amphiphilic property allows detergents to break protein-protein, protein-lipid and lipid-lipid associations, denature proteins and other macromolecules.

Targeting all 3 components of RNA viruses: genome RNA, lipid membrane, and envelope/nuclear proteins, this invention is to create an effective disinfectant system which applies the combination of RNases, proteases, and detergents, to eliminate the RNA viruses.

SUMMARY OF THE INVENTION

Targeting all 3 components of COVID 19 and all RNA viruses: genome RNA, lipid membrane, and envelope/nuclear proteins, the invention applies the combination of RNases, proteases, and detergents, at a broad concentration, pH, and temperature range, to eliminate the RNA viruses from any contaminated surfaces, creating an effective, convenient, environment friendly, and safe solution to disinfect RNA virus pathogens in concern.

DETAILED DESCRIPTION OF THE INVENTION

Figure 1:
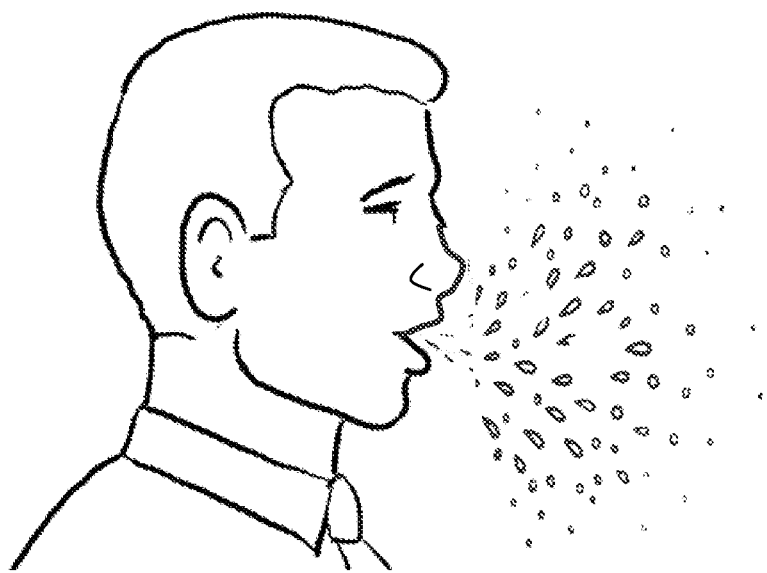
FIG. 1. Schematic photo of COVID 19 spread.
Figure 2:
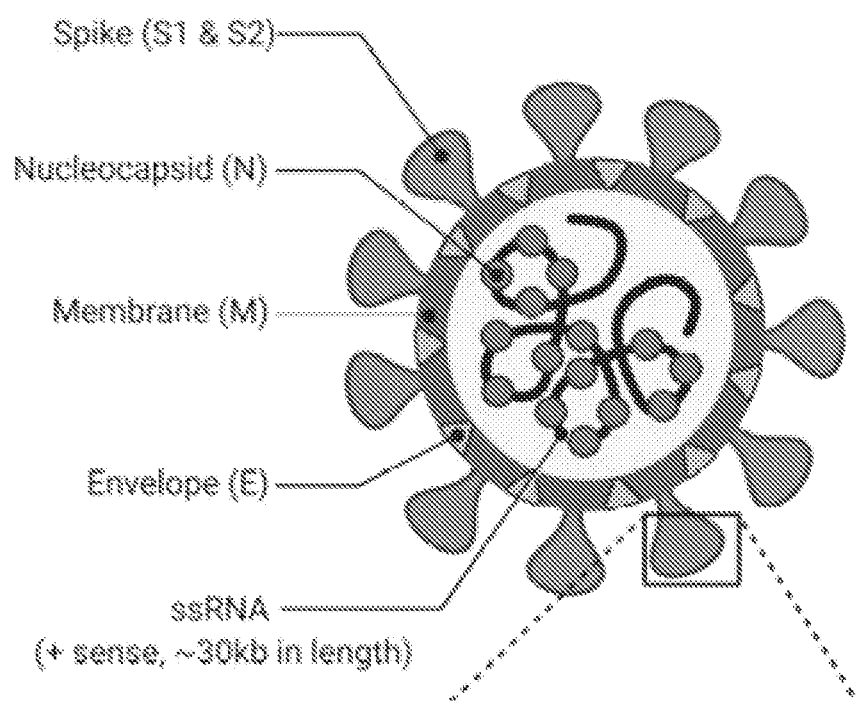
FIG. 2. Schematic Structure of COVID 19 (SARS-CoV-2) virus.
Figure 3:
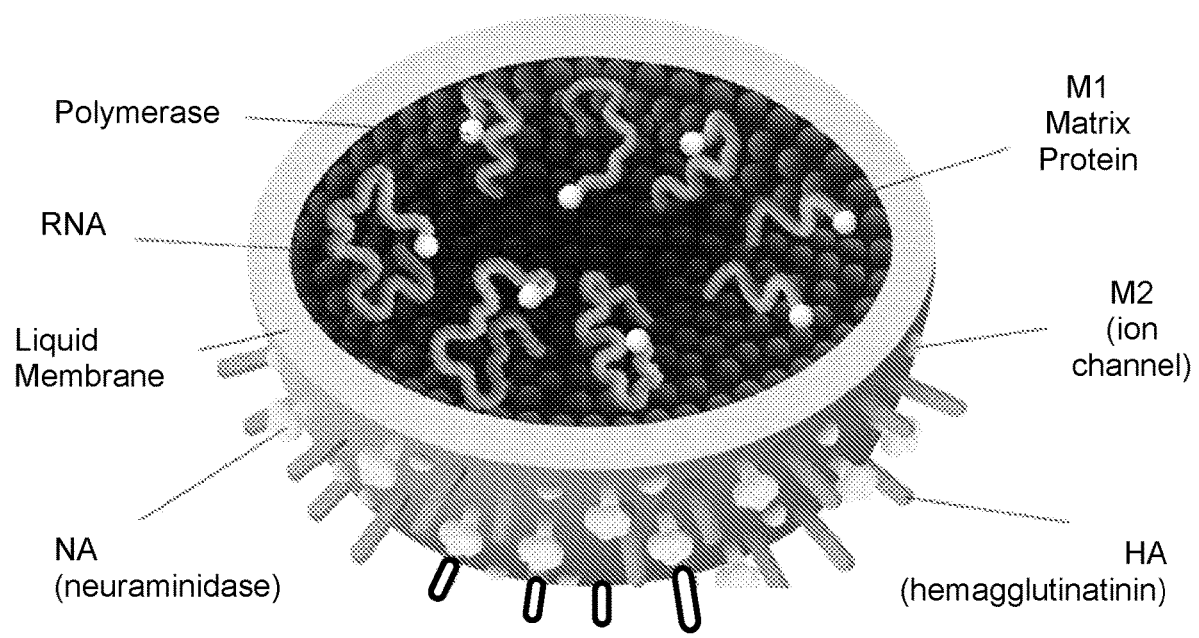
FIG. 3. Schematic Structure of Influenza virus. (Adapted from 123RM).

Ribonuclease A (RNase A) is a digestive enzyme secreted by the pancreas that specifically digests or hydrolyzes RNA polymers by endonuclease cleavage of the phosphodiester bonds forming the covalent links between adjacent ribonucleotide residues in these molecules.

RNase A is very stable, with its high measured enzyme activity towards single-stranded or double stranded RNA in the existence of up to 5% ionic or non-ionic detergents.

RNase A is active under a wide range of reaction conditions including low to high salt concentrations from 0 to 100 mM NaCl, wide range of temperatures from 15° C. to 80° C., and wide range of pH from 4.0 to 9.0.

The optimal working concentration of RNase A is 0.5 to 10 μg/mL, can go as low as 0.01 μg/mL, without apparent loss of enzyme activity.

Proteinase K is a broad-spectrum serine protease. It is well documented for its broad specificity and stability.

Proteinase K is commonly used for the destruction of proteins in cell lysates (tissue, cells) and membrane proteins for the release of nucleic acids (DNA and RNA).

Proteinase K is also stable over a wide pH range (4-12), with a pH optimum at 8.0.

An elevation of temperature from 37° C. to 65° C. increases the enzyme activity several times, with the addition of 0.5-1% sodium dodecyl sulfate (SDS). Proteinase K will not be inhibited by detergent such as Triton X100™, Tween 20™ and NP40™.

Detergents used in biomedical laboratories are mild surfactants (surface acting agents), used for the disruption of cell membranes and the release of intracellular materials.

Two major groups of detergents commonly used are ionic and non-ionic.

Ionic detergents are comprised of a hydrophobic chain and a charged head group which can be either anionic or cationic. They generally are stronger than non-ionic detergents and tend to be fairly harsh. Ionic detergents include: sodium dodecyl sulfate (SDS), sodium deoxy cholate, sodium cholate, sarkosyl.

Non-ionic detergents have uncharged hydrophilic head groups. They are considered mild surfactants as they break protein-lipid and lipid-lipid associations, but typically not protein-protein interactions, and generally, do not denature proteins.

Triton™ family. All members of the Triton™ family: Triton X-100™, Nonidet™ P-40 (NP-40™), Igepal® CA-630, are quite similar, differing slightly in their average number (n) of monomers per micelle and the size difference of their polyethylene glycol (PEG)-based head group.

Triton X100™ is on the Authorization List (Annex XIV) by the European Chemicals Agency (ECHA), for its potential impacts on human health and the environment. Nereid and Triton X100™ Reduced are the best replacement of Triton X100™ for biosafety after the "sunset date" Jan. 4, 2021, mandated by ECHA.

Tween™ family. Tween-20™ and Tween 80™ are polysorbate surfactants with a fatty acid ester moiety and a long polyoxyethylene chain. They are generally gentle surfactants, do not affect protein activity and are effective in solubilization.

This invention is the creation of an anti-RNA virus aqueous disinfectant, which mix up a variety of combinations from the RNases, Proteases, and detergents in a range of suitable concentrations of each component.

The aqueous disinfectant is intended to destroy all natural and/or naturally derived RNA viruses including COVID 19 and all known Corona viruses (SARS, MERS,) N1H1, HIV, as well as different types of influenzas.

A disinfectant mixture of an aqueous solution comprising from 0.01% to 5.0% wt/volume of an RNase and 0.01% to 5.0% wt/volume of a detergent is created as Part One (Part 1).

A second mixture of an aqueous solution comprising from 0.01% to 5.0% wt/volume of a Protease is created as Part Two (Part 2).

To maximize anti-virus effect of the disinfectant, Part 1 and Part 2 solutions are prepared separately. Part 1 is stored at low temperature; Part 2 is stored with Calcium Chloride as stabilizer. Mix the two parts right before usage, to minimize the loss of RNase activity, as well as autolysis of Protease.

A disinfectant mixture of an aqueous solution (Part 1) and (Part 2) was prepared in a Phosphate buffered Saline (PBS) or Tris-HCl buffer ranging from 1 mmol/L to 50 mmol/L, which provide a pH of between 6.0 to 9.0.

Unique autolysis feature of proteases in the system cleans the components after anti-virus reactions, making the complete disinfectant solution environmentally friendly, and biologically safe to use.

Example 1. An aqueous disinfectant solution comprising 0.5 ug/ml RNase A; 0.2 ug/ml Protease; 0.5 wt % Triton X100™, and a Tris-HCl buffer of 1 mmol/L, at pH of 7.0.

Example 2. An aqueous disinfectant solution comprising 0.1 ug/ml RNaseA; 0.05 ug/ml Protease; 0.5 wt % Triton X100™, and a Tris-HCl buffer of 1 mmol/L, at pH of 7.0.

Example 3. An aqueous disinfectant solution comprising 0.05 ug/ml RNaseA; 0.02 ug/ml Protease; 0.5 wt % Triton X100™, and a Tris-HCl buffer of 1 mmol/L, at pH of 7.0.

Example 4. An aqueous disinfectant solution comprising 0.01 ug/ml RNaseA; 0.01 ug/ml Protease; 0.5 wt % Triton X100™, and a Tris-HCl buffer of 1 mmol/L, at pH of 7.0.

Example 5. An aqueous disinfectant solution comprising 0.5 ug/ml RNaseA; 0.2 ug/ml Protease; 0.5 wt % NP40™, and a Tris-HCl buffer of 1 mmol/L, at pH of 7.0.

Example 6. An aqueous disinfectant solution comprising 0.1 ug/ml RNaseA; 0.05 ug/ml Protease; 0.5 wt % NP40™, and a Tris-HCl buffer of 1 mmol/L, at pH of 7.0.

Example 7. An aqueous disinfectant solution comprising 0.05 ug/ml RNaseA; 0.02 ug/ml Protease; 0.5 wt % NP40™, and a Tris-HCl buffer of 1 mmol/L, at pH of 7.0.

Example 8. An aqueous disinfectant solution comprising 0.01 ug/ml RNaseA; 0.01 ug/ml Protease; 0.5 wt % NP40™, and a Tris-HCl buffer of 1 mmol/L, at pH of 7.0.

Example 9. An aqueous disinfectant solution comprising 0.5 ug/ml RNaseA; 0.2 ug/ml Protease; 1.0 wt % Tween20™, and a Tris-HCl buffer of 1 mmol/L, at pH of 7.0.

Example 10. An aqueous disinfectant solution comprising 0.1 ug/ml RNaseA; 0.05 ug/ml Protease; 1.0 wt % Tween20™, and a Tris-HCl buffer of 1 mmol/L, at pH of 7.0.

Example 11. An aqueous disinfectant solution comprising 0.05 ug/ml RNaseA; 0.02 ug/ml Protease; 1.0 wt % Tween20™, and a Tris-HCl buffer of 1 mmol/L, at pH of 7.0.

Example 12. An aqueous disinfectant solution comprising 0.01 ug/ml RNaseA; 0.01 ug/ml Protease; 1.0 wt % Tween20™, and a Tris-HCl buffer of 1 mmol/L, at pH of 7.0.

Example 13. An aqueous disinfectant solution comprising 0.01 ug/ml RNaseA; 0.01 ug/ml Protease; 1.0 wt % SDS, and a Tris-HCl buffer of 1 mmol/L, at pH of 7.0.

Example 14. An aqueous disinfectant solution comprising 0.01 ug/ml RNaseA; 0.01 ug/ml Protease; 0.5 wt % SDS, and a Tris-HCl buffer of 1 mmol/L, at pH of 7.0.

Example 15. An aqueous disinfectant solution comprising 0.01 ug/ml RNaseA; 0.01 ug/ml Protease; 0.01 wt % SDS, and a Tris-HCl buffer of 1 mmol/L, at pH of 7.0.

Example 16. An aqueous disinfectant solution comprising 0.01 ug/ml RNaseA; 0.01 ug/ml Protease; 0.001 wt % SDS, and a Tris-HCl buffer of 1 mmol/L, at pH of 7.0.

The efficacy of the disinfecting composition described in Example 1 to Example 16 was demonstrated by human 28S (5070 nucleotides) and 18S (1869 nucleotides) RNA degradation either in vitro, or in vivo, in human lung carcinoma cell line A549.

All RNA degradation tests with A549 cells in vitro or in vivo were at room temperature.

Effective RNA degradation in the Example 1 to 16 is summarized in Table 1 and Table 2.

| RNase A | Protease | TritonX-100 (%) | RNA Integrity (%) |
|---|---|---|---|
| 0.5 ug/ml | 0.2 ug/ml | 0.5 | 0 |
| 0.1 ug/ml | 0.05 ug/ml | 0.5 | 0 |
| 0.05 ug/ml | 0.02 ug/ml | 0.5 | 0 |
| 0.01 ug/ml | 0.01 ug/ml | 0.5 | 0 |
| Negative control | | No RNase A | 100 |

| RNase A | Protease | NP40 (%) | RNA Integrity (%) |
|---|---|---|---|
| 0.5 ug/ml | 0.2 ug/ml | 0.5 | 0 |
| 0.1 ug/ml | 0.05 ug/ml | 0.5 | 0 |
| 0.05 ug/ml | 0.02 ug/ml | 0.5 | 0 |
| 0.01 ug/ml | 0.01 ug/ml | 0.5 | 0 |
| Negative control | | No RNase A | 100 |

| RNase A | Protease | Tween20 (%) | RNA Integrity (%) |
|---|---|---|---|
| 0.5 ug/ml | 0.2 ug/ml | 1 | 0 |
| 0.1 ug/ml | 0.05 ug/ml | 1 | 0 |
| 0.05 ug/ml | 0.02 ug/ml | 1 | 0 |
| 0.01 ug/ml | 0.01 ug/ml | 1 | 0 |
| Negative control | | No RNase A | 100 |

| RNase A | Protease | SDS | RNA Integrity (%) |
|---|---|---|---|
| 0.5 ug/ml | 0.2 ug/ml | 0.5 | 0 |
| 0.1 ug/ml | 0.05 ug/ml | 0.5 | 0 |
| 0.05 ug/ml | 0.02 ug/ml | 0.5 | 0 |
| 0.01 ug/ml | 0.01 ug/ml | 0.5 | 0 |
| Negative control | | No Rnase A | 100 |

Human A549 total RNA was prepared and used for in vitro RNA degradation.
$10^7$ A549 cell total RNA was used in each Example treatment at 25° C.
Disinfectant efficacy was evidenced by 28S and 18S human RNA integrity on RNA gel.

| RNase A | Protease | TritonX-100 (%) | RNA Integrity (%) |
|---|---|---|---|
| 0 | 0.2 mg/ml | 0.5 | 100 |
| 0.5 mg/ml | 0 | 0.5 | 0 |
| 0.5 mg/ml | 0.2 mg/ml | 0.5 | 0 |
| 0.1 mg/ml | 0.05 mg/ml | 0.5 | 0 |
| 0.05 mg/ml | 0.02 mg/ml | 0.5 | 0 |
| 0.01 mg/ml | 0.01 mg/ml | 0.5 | 0 |

| RNase A | Protease | NP40 (%) | RNA Integrity (%) |
|---|---|---|---|
| 0 | 0.2 mg/ml | 0.5 | 100 |
| 0.5 mg/ml | 0 | 0.5 | 0 |
| 0.5 mg/ml | 0.2 mg/ml | 0.5 | 0 |
| 0.1 mg/ml | 0.05 mg/ml | 0.5 | 0 |
| 0.05 mg/ml | 0.02 mg/ml | 0.5 | 0 |
| 0.01 mg/ml | 0.01 mg/ml | 0.5 | 100 |

| RNase A | Protease | Triton X100 (%) | RNA Integrity (%) |
|---|---|---|---|
| 0 | 0.02 mg/ml | 0.05 | 100 |
| 0.05 mg/ml | 0.02 mg/ml | 0.05 | 0 |
| 0.05 mg/ml | 0 | 0.05 | <10 |
| 0.01 mg/ml | 0.02 mg/ml | 0.05 | 0 |
| 0.01 mg/ml | 0 | 0.05 | <10 |

| RNase A | Protease | SDS | RNA Integrity (%) |
|---|---|---|---|
| 0 | 0.02 mg/ml | 0.05 | 100 |
| 0.05 mg/ml | 0.02 mg/ml | 0.05 | 0 |
| 0.05 mg/ml | 0 | 0.05 | <10 |
| 0.01 mg/ml | 0.02 mg/ml | 0.05 | 0 |
| 0.01 mg/ml | 0 | 0.05 | <10 |

Human A549 live cells were used for in vivo treatment to mimic intact virus particles.
$10^7$ A549 cells were treated in each listed Example condition at 25° C.
Live A549 cells were treated by RNase A without detergent and protease as control.
Total RNA was isolated at the stop in vivo treatment in each listed example.
Disinfectant efficacy was evidenced by 28S and 18S human RNA integrity on RNA gel.

Patent Citations (9)

| Patent Citations (9) | | | | |
|---|---|---|---|---|
| Publication number | Priority Date | Publication Date | Assignee | Title |
| US20070099283A1 | Feb. 8, 2002 | May 3, 2007 | Roche Diagnostics Operations Inc | Recombinant proteinase k |
| U.S. Pat. No. 7,368,274B2 | Feb. 9, 2001 | May 6, 2008 | Roche Diagnostics Operations Inc | Expression of recombinant proteinase K from Tritirachium album in yeast |
| U.S. Pat. No. 3,748,233A | Sep. 8, 1969 | Jul. 24, 1973 | Lever Brothers Co | Alkaline protease, method for its production, and detergent composition |
| U.S. Pat. No. 8,753,861B2 | Nov. 11, 2008 | Jan. 5, 2012 | Danisco US Inc | Protease comprising one or more combinable mutations |
| U.S. Pat. No. 8,173,409B2 | Dec. 30, 2004 | May 8, 2012 | Danisco US Inc | Acid fungal proteases |
| US20090259035A1 | Mar. 22, 2005 | Oct. 15, 2009 | RICHTER-HELM BIOLOGICS & Co KG GmbH | Method for producing recombinant RNase A |
| US20110287514A1 | Nov. 24, 2011 | Aug. 21, 2012 | University of California, Wisconsin Alumni Research Foundation | Cytotoxic ribonuclease variants |
| U.S. Pat. No. 5,268,289A | Dec. 27, 1991 | Dec. 7, 1993 | Epicentre Technologies Corp | Thermostable ribonuclease H |
| WO2019086463 | Oct. 30, 2017 | May 9, 2019 | Jean-Baptiste FARCET et al. | Environmentally compatible detergents for inactivation of lipid-enveloped viruses |

REFERENCES

Chen N, et al. (February 2020). Epidemiological and clinical characteristics of 99 cases of 2019 novel coronavirus pneumonia in Wuhan, China: a descriptive study. Lancet. 395 (10223): 507-513 Q&A on coronaviruses. World Health Organization. 8 Apr. 2020

Symptoms of Coronavirus. U.S. Centers for Disease Control and Prevention. 20 Mar. 2020

Hui D S, et al. (February 2020). The continuing 2019-nCoV epidemic threat of novel coronaviruses to global health—The latest 2019 novel coronavirus outbreak in Wuhan, China. Int J Infect Dis. 91: 264-66

New coronavirus stable for hours on surfaces. National Institutes of Health. 17 Mar. 2020. Archived from the original on 23 Mar. 2020. Retrieved 23 Mar. 2020

Doremalen N J, et al. (Apr. 16, 2020). Aerosol and Surface Stability of SARS-CoV-2 as Compared with SARS-CoV-1. New England Journal of Medicine 382:1564-1567.

Salehi S, et al (14 Mar. 2020). Coronavirus Disease 2019 (COVID-19): A Systematic Review of Imaging Findings in 919 Patients. American Journal of Roentgenology: 1-7

Lai C, et al (1 Mar. 2020). Severe acute respiratory syndrome coronavirus 2 (SARS-CoV-2) and coronavirus disease-2019 (COVID-19): The epidemic and the challenges. International Journal of Antimicrobial Agents. 55 (3): 105924

Lauer S A et al (10 Mar. 2020). The Incubation Period of Coronavirus Disease 2019 (COVID-19) From Publicly Reported Confirmed Cases: Estimation and Application. Annals of Internal Medicine. doi:10.7326/M20-0504. Retrieved 24 Mar. 2020

Bai Y et al (21 Feb. 2020). Presumed Asymptomatic Carrier Transmission of COVID-19. JAMA. 323 (14): 1406

Outbreak of severe acute respiratory syndrome coronavirus 2 (SARS-CoV-2): increased transmission beyond China—fourth update. European Centre for Disease Prevention and Control. 14 Feb. 2020. Retrieved 8 Mar. 2020

Andersen K G et al (17 Mar. 2020). The proximal origin of SARS-CoV-2. Nature Medicine. 26 (4): 450-452

Zhu N et al. (February 2020). A Novel Coronavirus from Patients with Pneumonia in China, 2019. The New England Journal of Medicine. 382 (8): 727-733

Coronavirus Disease 2019 (COVID-19)— Transmission. Centers for Disease Control and Prevention. 17 Mar. 2020. Retrieved 23 Mar. 2020.

Q&A on coronaviruses. World Health Organization. 11 Feb. 2020. Retrieved 13 Apr. 2020

Modes of transmission of virus causing COVID-19: implications for IPC precaution recommendations. World Health Organization Scientific Brief. Retrieved 29 Mar. 2020.

Collin E A et al (2015). Cocirculation of two distinct genetic and antigenic lineages of proposed influenza D virus in cattle. J Virol. 89 (2): 1036-42

Influenza (Seasonal). World Health Organization. 6 Nov. 2018. Archived from the original on 30 Nov. 2019. Retrieved 30 Nov. 2019

Longo D L (2012). "Chapter 187: Influenza". Harrison's principles of internal medicine (18th ed.). New York: McGraw-Hill Jefferson T et al. (July 2011). Physical interventions to interrupt or reduce the spread of respiratory viruses. Cochrane Database Syst Rev (7): CD006207

Up to 650 000 people die of respiratory diseases linked to seasonal flu each year. World Health Organization (Press release). 14 Dec. 2017. Archived from the original on 18 Apr. 2019. Retrieved 24 Sep. 2019.

Types of Influenza Viruses Seasonal Influenza (Flu). Centers for Disease Control and Prevention. 27 Sep. 2017. Retrieved 28 Sep. 2018

Mills C E et al (December 2004). Transmissibility of 1918 pandemic influenza. Nature. 432 (7019): 904-6.

Taubenberger J K et al (January 2006). 1918 Influenza: the mother of all pandemics. Emerging Infectious Diseases. 12 (1): 15-22.

Report of the Review Committee on the Functioning of the International Health Regulations (2005) in relation to Pandemic (H1N1) 2009. World Health Organization. 5 May 2011. p 37. Archived from the original on 14 May 2015.

Dawood F S et al. (September 2012). Estimated global mortality associated with the first 12 months of 2009 pandemic influenza A H1N1 virus circulation: a modelling study. The Lancet. Infectious Diseases. 12 (9): 687-95.

Kawaoka Y ed. (2006). Influenza Virology: Current Topics. Caister Academic Press. ISBN 978-1-904455-06-6. Archived from the original on 9 May 2008

Vainionpää R et al (April 1994). Biology of parainfluenza viruses. Clin. Microbiol. Rev. 7 (2): 265-75

Cuchillo C M et al (September 2011). Bovine pancreatic ribonuclease: fifty years of the first enzymatic reaction mechanism. Biochemistry. 50 (37): 7835-41.

Dyer K D et al (November 2006). The RNase a superfamily: generation of diversity and innate host defense. Molecular Diversity. 10 (4): 585-97.

King J V et al (2014-07-08). "Molecular basis of substrate recognition and degradation by human presequence protease". Structure. 22 (7): 996-1007.

Shen Y et al (2006-10-19). "Structures of human insulin-degrading enzyme reveal a new substrate recognition mechanism". Nature. 443 (7113): 870-874

Rawlings N D et al (February 1993). Evolutionary families of peptidases. The Biochemical Journal. 290 (Pt 1): 205-18.

Linke D. (2009) Detergents: an overview. Methods Enzymol. 463: 603-17

Luche S et al (2003). Evaluation of nonionic and zwitterionic detergents as membrane protein solubilizers in two-dimensional electrophoresis. Proteomics. 3: 249-53

Chae P et al. (2012) A new class of amphiphiles bearing rigid hydrophobic groups for solubilization and stabilization of membrane proteins. Chemistry. 18:9485-90

Raines R T (1998). Ribonuclease A. Chem. Rev. 98 (3): 1045-1066.

Richards F M (1972). The 1972 nobel prize for chemistry. Science. 178 (4060): 492-3

Marshall G R et al (2008). Back to the future: Ribonuclease A. Biopolymers. 90 (3): 259-77

Morihara K et al (1975). Specificity of proteinase K from Tritirachium album Limber for synthetic peptides. Agric. Biol. Chem. 39 (7): 1489-1492.

Hilz H et al (1975). Stimulation of Proteinase K action by denaturing agents: application to the isolation of nucleic acids and the degradation of 'masked' proteins. European Journal of Biochemistry. 56 (1): 103-108.

Suzuki H et al (1988). Removal of dodecyl sulfate from protein solution. Anal Biochem. 172: 259-63

Bales B L et al (1998). Precision Relative Aggregation Number Determinations of SDS Micelles Using a Spin Probe. A Model of Micelle Surface Hydration. J. Phys. Chem. B. 102 (50): 10347-58

Johnson M (2018). Detergents: Triton X-100, Tween-20, and More. Materials and Methods. 3: 163-72

Farcet J B et al (12 Dec. 2019). Development of a Triton X-100 replacement for effective virus inactivation in biotechnology processes. Engineering Reports. 1 (5).

Authorization List. European Chemicals Agency. Retrieved Dec. 14, 2019.

Koley D et al (2010). Triton X-100 concentration effects on membrane permeability of a single HeLa cell by scanning electrochemical microscopy (SECM). Proc. Natl. Acad. Sci. U.S.A. 107 (39): 16783-7.

Sinha S et al (2017). Use of substitute Nonidet P-40 nonionic detergents in intracellular tubulin polymerization assays for screening of microtubule targeting agents. Biochemistry and Cell Biology. 95 (3): 379-384.

Ayorinde F O et al (2000). Analysis of some commercial polysorbate formulations using matrix-assisted laser desorption/ionization time-of-flight mass spectrometry. Rapid Communications in Mass Spectrometry. 14 (22): 2116-2124.

Chen X L et al (2013) Rapid monitoring of autolysis process of proteases by capillary electrophoresis. Biotechnology Letters. 25: 1763-1767.

What is claimed is:

1. A disinfectant solution comprising a first aqueous solution comprising 0.01 or 0.05 µg/mL of ribonuclease A (RNase A) and 0.001 or 0.01% w/v of a detergent selected from the group consisting of sodium dodecyl sulfate (SDS) and nonyl phenoxypolyethoxyethanol-40, and a second aqueous solution comprising proteinase K at a concentration of about 0.01, 0.02, 0.05, or 0.2 µg/mL, wherein the first aqueous solution and the second aqueous solution are formulated to be combined immediately prior to use to yield said disinfectant solution.

2. A method of eliminating RNA viruses from a contaminated surface, the method comprising contacting said surface with the disinfectant solution of claim 1, wherein the RNA viruses are thereafter eliminated from the contaminated surface.

3. The method of claim 2, wherein the RNA viruses are selected from one or more of natural RNA viruses, naturally derived RNA viruses, or both.

4. The method of claim 2, wherein the RNA viruses are selected from one or more of Severe Acute Respiratory Syndrome-related coronavirus (SARS-CoV-2), Middle East Respiratory Syndrome (MERS), Swine flu (H1N1), Human Immunodeficiency Virus (HIV), and Influenza virus.

5. The method of claim 2, wherein the disinfectant solution is configured to target genomic RNA, lipid membrane, and envelope/nuclear proteins of said RNA viruses.

6. The disinfectant solution of claim 1, wherein the solution has a pH in the range of pH 6 to pH 9.

7. The method of claim 2, wherein the step of contacting is performed at room temperature.

8. The disinfectant solution of claim 1, wherein the second aqueous solution further comprises calcium chloride.

\* \* \* \* \*